United States Patent [19]

Stahl et al.

[11] Patent Number: 5,616,773
[45] Date of Patent: Apr. 1, 1997

[54] PREPARATION OF 5-CYANOVALERATES

[75] Inventors: Stefan Stahl, Worms; Wolfgang Harder, Weinheim; Arthur Hoehn, Kirchheim, all of Germany

[73] Assignee: BASF Aktiengesellschaft, Ludwigshafen, Germany

[21] Appl. No.: 419,608

[22] Filed: Apr. 10, 1995

Related U.S. Application Data

[63] Continuation-in-part of Ser. No. 203,022, Feb. 28, 1994, Pat. No. 5,434,290.

[30] Foreign Application Priority Data

Mar. 3, 1993 [DE] Germany ............ 43 06 507.4

[51] Int. Cl.$^6$ ............................................. C07C 255/03
[52] U.S. Cl. ............................................. 558/353
[58] Field of Search ............................................. 558/353

[56] References Cited

U.S. PATENT DOCUMENTS 4,950,778  8/1990  Burke et al. ............ 558/353
5,434,290  7/1995  Stahl et al. ............ 558/353

*Primary Examiner*—Johann Richter
*Assistant Examiner*—John Peabody
*Attorney, Agent, or Firm*—Keil & Weinkauf

[57] ABSTRACT

Preparation of 5-cyanovalerates (I) by the carbonylation of a 1-cyanobutene with carbon monoxide and an alkanol (II) corresponding to the ester radical at an elevated temperature and under superatmospheric pressure in the presence of a cobalt catalyst as well as in the presence of an activating solvent, in which the activating solvent used is an effective amount of a urea of the formula IIIc $$R_2N-CO-NR_2 \qquad (IIIc)$$

where R is, $C_1$–$C_6$-alkyl, $C_5$–$C_7$-cycloalkyl or where 2R groups together form 5-membered to 7-membered rings. The end products I serve as intermediates, chiefly for the preparation of ε-caprolactam.

4 Claims, No Drawings

PREPARATION OF 5-CYANOVALERATES

The instant application is a continuation-in-part of application Ser. No. 08/203,022, filed Feb. 28, 1994, now U.S. Pat. No. 5,434,290.

The present invention relates to an improved process for the preparation of 5-cyanovalerates (I) by the carbonylation of a 1-cyanobutene with carbon monoxide and an alkanol (II) corresponding to the ester radical at an elevated temperature and under superatomospheric pressure in the presence of a cobalt catalyst as well as in the presence of a urea activating solvent.

According to the general teaching of EP-A 373,570, it is known to be possible to convert 1-cyanobutenes to 5-cyanovaleric acid or to the alkyl esters of these acids by carbonylation with carbon monoxide and water or an alkanol under elevated pressure and temperature conditions using cobalt catalysts, this reaction being carried out in the presence of from 70 to 99 wt %, based on the weight of the reaction mixture, of a lactam or cyclic urea derivative acting as activating solvent. As far as the preparation of the esters is concerned, this reaction is described only with reference to the methyl ester using the lactam N-methylpyrrolidone, but the conversion of 12.9% achieved by this process is unsatisfactory.

It is thus an object of the present invention to make the alkyl esters of 5-cyanovaleric acid more readily available than hitherto. In particular, activating solvents are required which show a favorable action even at a relative low concentration.

Accordingly, we have found an improved process for the preparation of a 5-cyanovalerate (I) by the carbonylation of a 1-cyanobutene with carbon monoxide and an alkanol (II) corresponding to the ester radical, at an elevated temperature and under superatomospheric pressure in the presence of a cobalt catalyst and in the presence of an activating solvent, wherein the activating solvent used comprises an effective amount of a urea of the formula IIIc

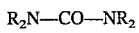

in which the radicals R may be the same or different and stand for $C_1$–$C_6$-alkyl groups or $C_5$–$C_7$-cycloalkyl groups, which radicals can be interconnected to form 5-membered to 7-membered rings.

The reaction can be illustrated as follows:

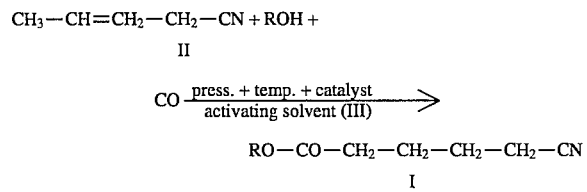

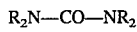

R = alkyl

The 1-ene and 3-ene isomer or, if desired, isomer mixtures can be used instead of cyanobut-2-ene, since the isomers assume a state of equilibrium under the reaction conditions. Also both the trans- and cis-isomers of cyanobut-1-ene and cyanobut-2-ene are suitable for use as starting compounds for the process of the invention. For economical reasons, it is preferred to use cyanobut-2-ene, which is readily obtainable by adding hydrogen cyanide to butadiene.

The success of the process of the invention is not basically dependent on the alkanols ROH (II). Thus $C_1$–$C_2$-alkanols are suitable, of which $C_1$–$C_4$-alkanols are preferred, especially methanol and ethanol.

For each mole of 1-cyanobutene there will normally be used from 0.5 to 10 mol and preferably from 1 to 5 mol of the alkanol II. Substoichiometric amounts of alkanol are recommendable when the conversion of the cyanobutene should be restricted in order, for example, to raise the selectivity toward the desired end product (I).

An essential feature of the process of the invention is the co-use of the activating solvent IIIc defined above, $$R_2N\text{---}CO\text{---}NR_2 \qquad (IIIc)$$

in which the radicals R can be the same or different and stand for $C_1$–$C_6$-alkyl groups or $C_5$–$C_7$-cycloalkyl groups, which radicals can be interconnected to form 5-membered to 7-membered rings.

Suitable ureas IIIc are cyclic urea derivatives such as N,N'-dimethylethylene urea, N,N'-diethylethylene urea, and N,N'dimethylpropylene urea as well as primarily, open-chained compounds such as N,N,N',N'-tetramethyl urea and N,N,N',N'-tetraethyl urea.

The amount used of activating solvent is preferably kept to a minimum. The initial concentration of the activating solvents in the total reaction mixture can be from 35 to 65 wt % and preferably is from 40 to 50 wt %.

Above said range, there are obtained mostly good selectivities toward the straight-chain 5-cyanovalerates, but this is at the expense of a reduction of the space-time yield of the reaction and the cost of purification increases.

The reaction can alternatively be carried out in the presence of further organic solvents, provided they are inert under the reaction conditions. For example, hydrocarbons are suitable such as n-pentane, n-hexane, toluene, and the xylenes, in addition to esters, e.g., tetrahydrofuran, dioxane, or ethylene glykol dimethyl ether, as well as carboxylates such as methyl acetate, ethyl acetate, and butyl acetate.

In other respects, the carbonylation is carried out in conventional manner, i.e., at temperatures ranging from 130° to 200° C. and preferably from 140° to 190° C. and under a pressure of from 50 to 700 bar and preferably from 100 to 350 bar.

Preferably, pure carbon monoxide is used for the reaction, but the presence of hydrogen, in a concentration which should be lower than 10 vol %, depending on the particular embodiment of the process of the invention, can also effect activation of the cobalt catalyst.

Suitable cobalt catalysts are dicobalt octacarbonyl or cobalt carbonyl hydrogen.

Instead of these carbonyl complexes it is also possible to use salts such as cobalt acetate, cobalt formate, or cobalt-2-ethyl hexanoate, but most preferably the cobalt salts of those carboxylic acids which can be produced in minor quantities during the reaction as by-products, such as, for example, cobalt valerate, cobalt adipate, or cobalt methyl glutarate. These salts convert to the active complexes under the reaction conditions in situ.

The concentration of the catalysts is usually from 0.1 to 5 wt % and preferably from 0.3 to 3 wt % of cobalt, based on the total weight of the reaction mixture.

The formation of a catalytically effective cobalt compound can be accelerated by the addition of water, preferably used in an amount of from 0.5 to 4 mol per mole of cobalt.

The process may be carried out batchwise or continuously by conventional techniques.

To achieve satisfactory selectivities toward the end product I the reaction is preferably carried out up to a conversion of from 35 to 70%, based on the 1-cyanobutene.

The purification of the reaction mixture is carried out in known manner, preferably by fractional distillation. The solvents and starting compounds thus obtained are advantageously recycled to the carbonylation.

The linear cyanates are usually obtained in selectivities of from 80 to 90%, based on 50% conversion of the 1-cyanobutene. There are also formed approximately from 0.5 to 5% chiefly of dialkyl adipates derived from the alkanols II, and from 0.5 to 8% of valeronitrile as well as small amounts of other by-products.

The process of the invention has the advantage that even when use is made of relatively small amounts of the said activating solvent IIIc surprisingly high selectivities toward the straight-chain 5-cyanovalerates (I) are achieved.

The esters of 5-cyanovaleric acid produced by the method of the invention are precursors for ε-caprolactam which is of significance in the preparation of polyamides.

EXAMPLES

EXAMPLE 1

An autoclave having a capacity of 107 mL was filled with a solution of 27.2 wt % of 1-cyanobut-2-ene 21.2 wt % of methanol 48.2 wt % of N,N,N',N'-tetramethylurea 2.8 wt % of $Co_2(CO)_8$, and 0.6 wt % of water.

10.3 g/h of the same solution and 1.72 L/h (STP) of carbon monoxide gas were then continuously added under a CO pressure of approximately 200 bar and at a temperature of 160° C. and the continuously discharged effluent was subjected to gas-chromatographic analysis (internal standard benzonitrile).

The following results were achieved(GC):
conversion of the cyanobutene: 47%
selectivity toward cyanates: 89% proportion thereof toward I(n-portion):98%
The effluent was worked up by distillation in the usual manner.

EXAMPLE 2

The experiment was carried out in a manner similar to Example 1, except that 8.9 g/h of a solution of 27.2 wt % of 1-cyanobut-2-ene 21.2 wt % of methanol 48.2 wt % of N,N'-dimethylpropylene urea 2.8 wt % of $Co_2(CO)_8$, and 0.6 wt % of water ps and 1.72 L/h (STP) of carbon monoxide gas were caused to react.

The following results were achieved (GC):
conversion of the cyanobutene: 39%
selectivity toward cyanates: 89% proportion thereof toward I(n-portion): 96%

Comparative Example A

The experiment was carried out analogously to Example 1, with the exception that 9.9 g/h of a mixture of 13.0 wt % of 1-cyanobut-2-ene 10.1 wt % of methanol 75.3 wt % of N,N,N',N'-tetramethylurea (TMU)

1.35 wt % $Co_2(CO)_8$ 0.25 wt % water and 1.72 l/h CO was used. The results are given in Table 1.

Comparative Example B

The experiment was carried out analogously to Example 1, with the exception that 9.2 g/h of a mixture of 16.0 wt % of 1-cyanobut-2-ene 12.4 wt % of methanol 69.9 wt % of N,N'-dimethylpropylene urea (DMPU)

1.70 wt % $Co_2(CO)_8$ 0.30 wt % water and 1.72 l/h CO was used. The results are given in Table 1.

TABLE 1

| Example | Solvent | Selectivity to 5-CVE | conversion | Space-time-yield |
|---|---|---|---|---|
| 1 | TMU 48.2 wt % | 87% | 47% | 18 g/l/h |
| A | TMU 75.3 wt % | 85% | 2% | 0.3 g/l/h |
| 2 | DMPU 48.2 wt % | 85% | 39% | 14 g/l/h |
| B | DMPU 69.6 wt % | 88% | 3% | 2.2 g/l/h |

5-CVE = methylester of 5-cyanovaleric acid conversions of the cyanobutene

Examples C to F

An autoclave having a capacity of 300 mL was filled with a solution of N,N-dimethylpropylene urea (DMPU), 1-cyanobut-2-ene, methanol and $Co_2(CO)_8$ in amounts given in Table 2. Then the autoclave was pressurized with carbon monoxide (100 bar) and heated to 160° C. After the temperature was reached, the CO pressure was raised to 210 bar for 4 hours. Then the autoclave was cooled and depressurized. After that the content of the autoclave was subjected to gas-chromatographic analysis (internal standard benzonitrile). The following results were achieved (see Table 2):

TABLE 2

| Example | DMPU [g] | 1-cyano-but-2-ene [g] | MeOH [g] | $Co_2(CO)_8$ [g] | DMPU [wt %] | Conv. [1%] | Sel. [%] | Yield [%] |
|---|---|---|---|---|---|---|---|---|
| C | 47.3 | 36.5 | 36.0 | 6.3 | 38 | 39 | 17 | 7 |
| D | 42.0 | 24.3 | 24.0 | 4.2 | 44 | 53 | 44 | 24 |
| E | 52.5 | 24.3 | 24.0 | 4.2 | 50 | 70 | 66 | 47 |
| F | 90.0 | 24.3 | 24.0 | 4.2 | 63 | 42 | 68 | 29 |

Conv. = conversion of the cyanobutene
Sel. = selectivity toward 5-CVE
Yield toward 5-CVE

We claim:

1. A process for the preparation of a 5-cyanovalerate (I) by the carbonylation of a 1-cyanobutene with carbon monoxide and a $C_1$–$C_{12}$-alkanol (II) corresponding to the ester radical, at a temperature of from 130° to 200° C. and under superatomospheric pressure in the presence of a cobalt catalyst selected from the group consisting of dicobalt octacarbonyl, cobalt carbonyl hydrogen, cobalt acetate, cobalt formate, cobalt-2-ethyl hexanote, cobalt valerate, cobalt adipate and cobalt methyl glutarate and in the presence of an activating solvent of the formula III $$R_2N\text{—}CO\text{—}NR_2 \qquad \text{III}$$

in which the radicals R may be the same or different and stand for $C_1$–$C_6$-alkyl groups which may be interconnected to form a cyclic urea having a 5-membered to 7-membered ring or $C_5$–$C_7$-cycloalkyl groups, the initial concentration of the activating solvent in the total reaction mixture being from 35 to 65 wt %.

2. A process of claim 1, wherein the initial concentration of the activating solvent in the total reaction mixture being from 40 to 50 wt %.

3. A process of claim 1, wherein the alkanol (II) is methanol or ethanol.

4. A process of claim 2, wherein the alkanol (II) is methanol or ethanol.

* * * * *

UNITED STATES PATENT AND TRADEMARK OFFICE
CERTIFICATE OF CORRECTION

PATENT NO.: 5,616,773

DATED: April 1, 1997

INVENTOR(S): STAHL et al.

It is certified that error appears in the above-identified patent and that said Letters Patent is hereby corrected as shown below:

Column 5, claim 1, line 6, "atomospheric" should be --atmospheric--.

Signed and Sealed this

Seventeenth Day of June, 1997

Attest:

BRUCE LEHMAN

Attesting Officer

Commissioner of Patents and Trademarks